United States Patent [19]

Eger, II et al.

[11] Patent Number: 4,881,541

[45] Date of Patent: Nov. 21, 1989

[54] VAPORIZER FOR AN ANESTHETIC HAVING A VAPOR PRESSURE ABOUT ONE ATMOSPHERE

[75] Inventors: Edmond I. Eger, II, San Francisco; Brynte H. Johnson, San Ramon, both of Calif.

[73] Assignee: The Regents of the University of California, Oakland, Calif.

[21] Appl. No.: 287,721

[22] Filed: Dec. 21, 1988

[51] Int. Cl.$^4$ ............................................. A61M 15/00
[52] U.S. Cl. ........................... 128/203.25; 128/203.26; 128/203.27; 128/204.17; 128/203.14; 137/625.3
[58] Field of Search ....................... 128/203.25, 204.29, 128/203.24, 203.21, 204.14, 204.21, 204.18, 203.12, 203.14, 204.17, 204.13; 131/625.29, 625.3, 599

[56] References Cited

U.S. PATENT DOCUMENTS

| | | | |
|---|---|---|---|
| 3,534,732 | 10/1970 | Bickford | 128/203.14 |
| 3,575,168 | 4/1971 | Jones et al. | 128/203.14 |
| 3,651,805 | 3/1972 | Breiling | 128/203.14 |
| 3,703,172 | 11/1972 | Hay | 128/204.17 |
| 3,714,391 | 1/1973 | Katzman et al. | 128/203.17 |
| 3,841,560 | 10/1974 | Sielaff | 128/203.25 |
| 4,017,566 | 4/1977 | Seidel | 128/203.14 |
| 4,067,935 | 1/1978 | Jones et al. | 128/203.14 |
| 4,075,297 | 2/1978 | Seidel | 128/204.13 |
| 4,477,395 | 10/1984 | Albarda | 128/203.14 |
| 4,564,748 | 1/1986 | Gupton | 128/204.17 |
| 4,587,966 | 5/1986 | Albarda | 128/204.17 |
| 4,607,634 | 8/1986 | Clapham | 128/203.25 |
| 4,719,910 | 1/1988 | Jensen | 128/204.25 |

FOREIGN PATENT DOCUMENTS 1307905 2/1973 United Kingdom.

OTHER PUBLICATIONS

H. G. Epstein, et al., Oxford Vaporizer No. 2, *The Lancet*, pub. Jul. 19, 1941, pp. 64–66.
A. G. Dobkin & A. R. Hunter, "Vaporizeres for Inhalation Anesthetics", *Development of New Volatile Inhalation Anesthetics*, 38 1979, pp. 311–341.
J. A. Dorsch and S. E. Dorsch, "Vaporizers, Chapter 4", *Understanding Anesthesia Equipment: Construction, Care and Complications*, 2d Ed. 1984, pp. 77–135.

*Primary Examiner*—Eugene M. Eickholt
*Attorney, Agent, or Firm*—Phillips, Moore, Lempio & Finley

[57] ABSTRACT

The present invention relates to an apparatus useful to controllably vaporize and mix a volatile anesthetic, having a vapor pressure of about 760 mm of mercury at about 20° C., into an effective anesthetic/diluent gas mixture to be administered to a mammal. More specifically, the present invention is an apparatus, of interconnected components including anesthetic in a canister, diluent gas supply, flow meters, tubing connections, mixing carburetor, heating means, thermoelectric temperature control means, and the like. These components are maintained within a temperature controlled chamber such that the volatile anesthetic/diluent gas is effectively and controllably delivered to the patient. A preferred anesthetic is I-653, $CF_3H—O—CFH—CF_3$.

20 Claims, 3 Drawing Sheets

FIG._1
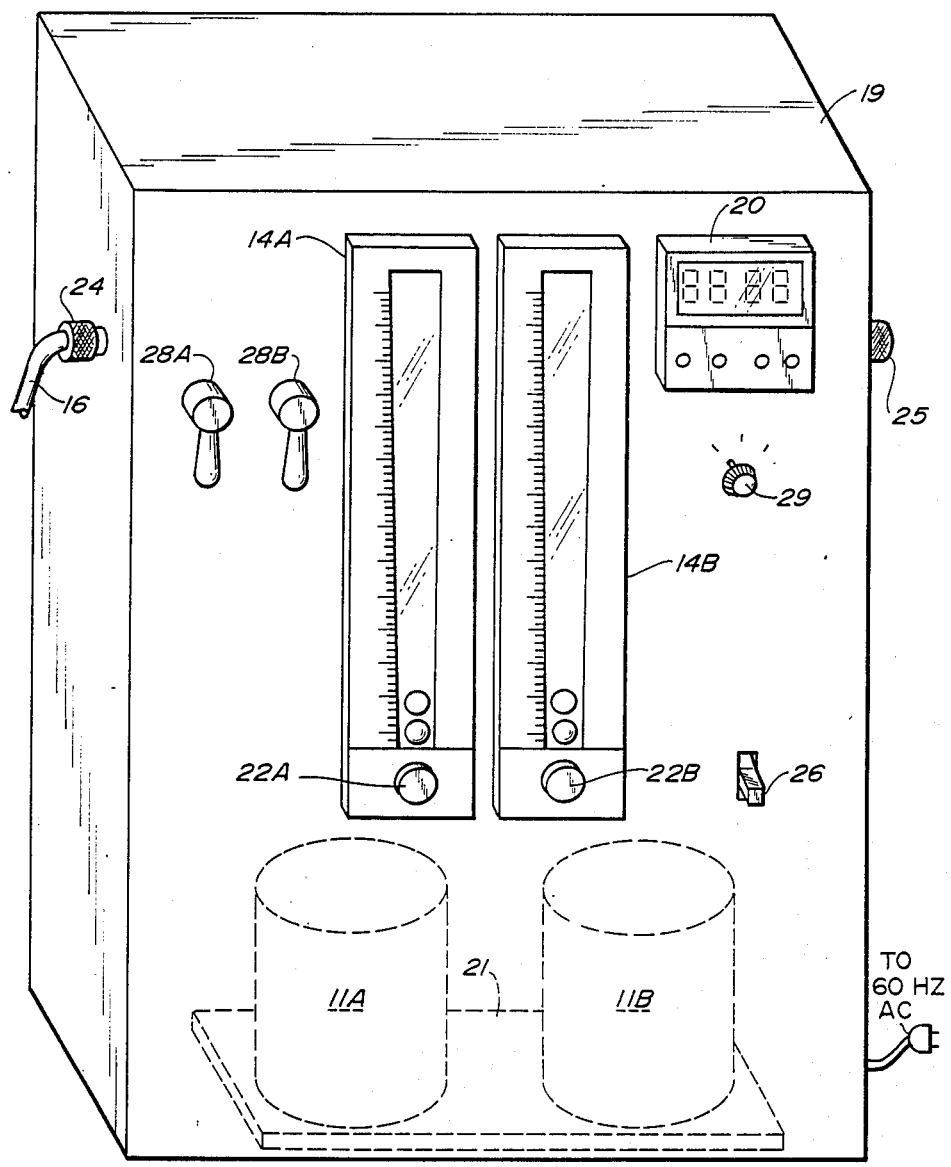

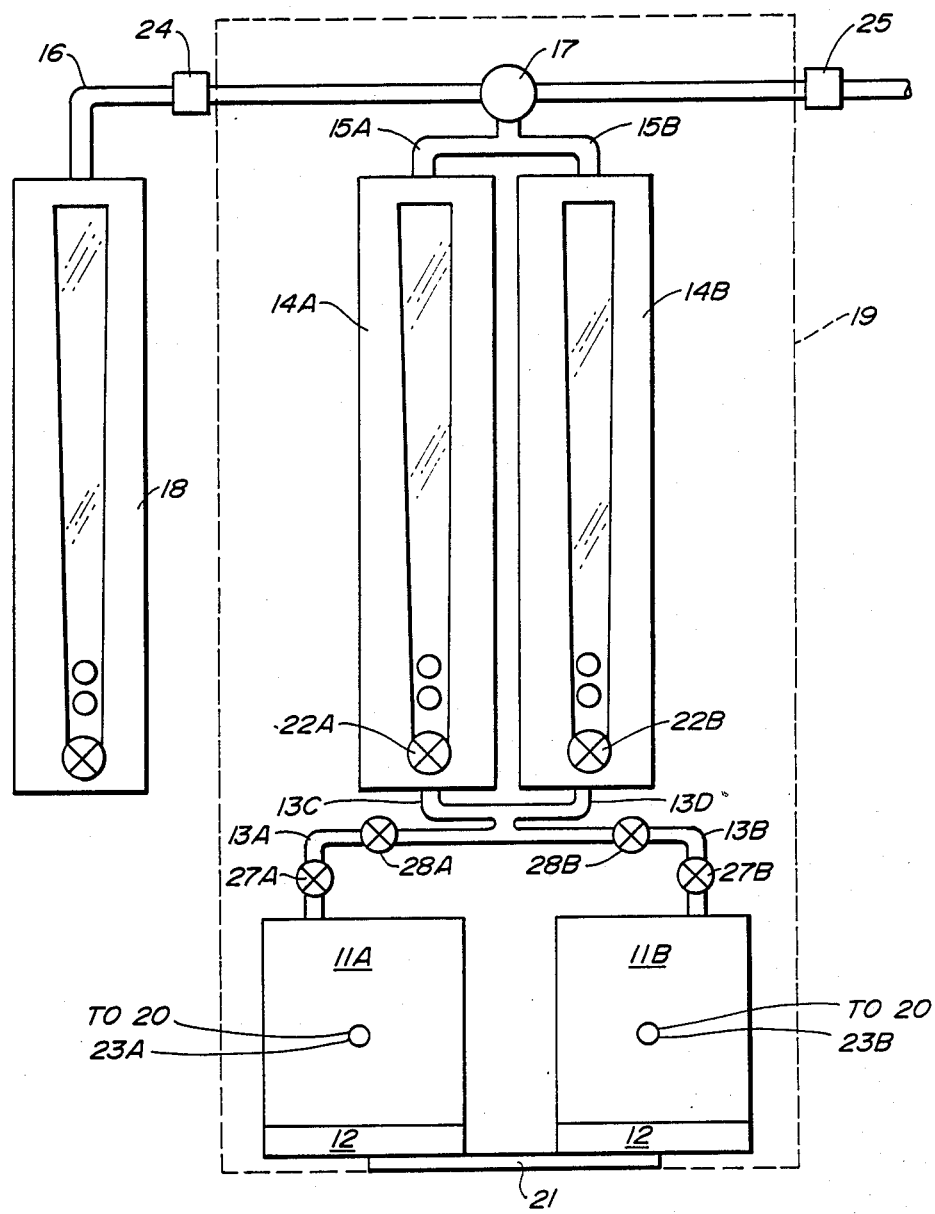
FIG._2

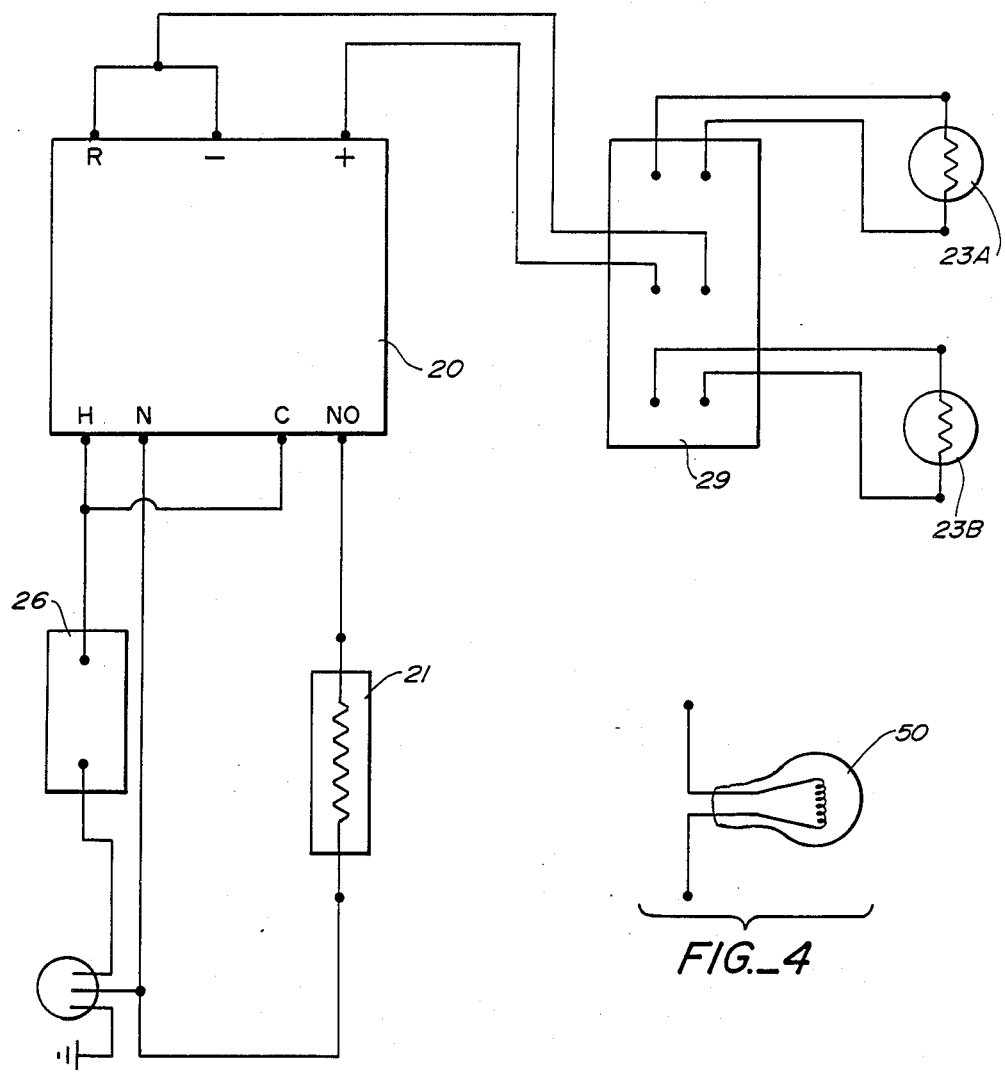
FIG._3
FIG._4

VAPORIZER FOR AN ANESTHETIC HAVING A VAPOR PRESSURE ABOUT ONE ATMOSPHERE

BACKGROUND OF THE INVENTION

1. Field of Invention

The present invention relates to an apparatus useful to controllably volatilize and mix a volatile anesthetic, having vapor pressure of about 760 mm of mercury at about 20° C. into an effective anesthetic/diluent gas mixture to be administered to a mammal. More specifically, the invention is an apparatus to volatilize an inhalation anesthetic of structure, $CF_2H-O-CFH-CF_3$, I—653, and a diluent gas, to a human being.

2. Description of Related Art

Anesthetic vaporizers of the art useful to vaporize currently used and experimental liquid inhalation anesthetics having low vapor pressures:

| Anesthetic | B.P., °C. | Vapor Pressure (at °C.) |
|---|---|---|
| Halothane | 50. | 243 Torr |
| Methoxyflurane | 104.65 | 23 |
| Enflurane | 56.5 | 175 |
| Isoflurane | 48.5 | 238 |
| (but not including) | | |
| I-653 (Experimental) | 23.5 | 664 |

The vaporizers of the art act for liquid inhalation anesthetics as "humidifiers" to vaporize and entrain the vaporized anesthetic. These machines come in a number of configurations, e.g., variable bypass vaporizers, measured flow vaporizers, bubble-through vaporizers, etc.

Gaseous inhalation anesthetics, such as nitrous oxide, cyclopropane, ethylene etc., are delivered satisfactorily and accurately using only a flowmeter, and generally do not need to be heated.

I—653 because of its boiling point liquifies or vaporizes so easily at ambient temperature, that the accurate delivery of the anesthetic as a gas is very difficult or impossible using the above conventional vaporizers.

An overview of the vaporizers used in inhalation anesthetics is found in "Vaporizers, Chapter 4", of *Understanding Anesthesia Equipment: Construction, Care and Complications,* Second Edition, by J. A. Dorsch and S. E. Dorsch, published by Williams and Wilkins of Los Angeles, Calif. in 1984, pp. 77-135.

Dorsch et al. describe various methods used to supply heat to keep the temperature of the volatile anesthetic liquid constant for accurate delivery. These methods include the following:

(a) Construct the vaporizer of a large mass of copper to conduct heat easily from ambient air or operating tabletop.

(b) Using wicks in direct contact with metal (increases the surface contact only). This does not aid in temperature control but only increases the efficiency of vaporization.

(c) Use of a water jacket—but this method proved to be rather inefficient.

(d) Using an electric heater inside the vaporizer. This method adds problems which make its practical use complicated so that no anesthetic vaporizers with this feature are currently being produced.

A similar discussion of the art is summarized by A. B. Dobkin and A. R. Hunter in Chapter 11; "Vaporizers for Inhalation Anesthetics," in *Development of New Volatile Inhalation Anesthetics,* Dobkin (ed.) published by Elsevier/North-Holland Biomedical Press, in 1979, pp. 311-341.

Some U.S. patents of general interest, for example: W. Jones, U.S. Pat. No. 3,575,168; H. G. Breiling, U.S. Pat. No. 3,651,805; W. H. Hay, U.S. Pat. No. 3,703,1772; U. Sielaff, U.S. Pat. No. 3,841,560; P. Seidel, 4,017,566; P. Seidel, U.S. Pat. No. 4,075,297; S. Albarda, U.S. Pat. No. 4,587,066; and T. R. Clapham, U.S. Pat. No. 4,807,634.

United Kingdom Pat. No. 1,307,905 issued to S.A.C.-C.A.B., S.P.A., an Italian company, is also of general interest.

More specifically, H. G. Epstein, et al disclose the "Oxford Vaporizer No. 2, in *The Lancet,* pp. 64-66, in the issue dated Jul. 19, 1941. This inhalation anesthetic vaporizer uses the latent heat of fusion of an organic compound, e.g. para-dichlorobenzene (m.p. +52° C.), to maintain a constant temperature for the anesthetic.

S. R. Wilson et al. disclose a "New Invention-A Warm Ether Bomb" in *The Lancet,* published Feb. 12, 1921, p. 366. This apparatus simply heats the liquid ether so that it will self delivery as a warm gas to the patient. The apparatus needs to withstand a pressure of about 250 pounds per square inch, and the anesthetic gas is delivered to a face mask at between 90° and 98° F.

All of the references cited in this application are incorporated herein by reference.

After examination of the above patents and articles, it is apparent that none of the references, individually or collectively, teach or disclose a method of precisely controlling the vapor of a volatile anesthetic having a vapor pressure about one atmosphere at about 15° to 30° C. (The temperature range present in most operating rooms.)

In the evaluation of a new inhalation anesthetic (having a vapor pressure of about one atmosphere) (e.g. $CF_2H-O-CFHCF_3$), called I—653 by its producer, Anaquest (a subsidiary of British Oxygen Corporation) of 2005 W. Beltline Highway, Madison, Wis. 53713), it became rapidly apparent that the conventional inhalation anesthetic vaporizers could not be directly used. To function in any reasonable manner, required extensive modifications to produce the medically required controllable concentration of gaseous anesthetic. In a warm room (in excess of 24° C.), I—653 boils thus producing a 100% concentration of gaseous anesthetic. In a cool room (e.g. 20° C. or less), vaporization of I—653 using conventional inhalation anesthetic vaporizers produce a vapor concentration that varies enormously depending upon the temperature. Even a temperature change of 1° C. can produce a significant vapor change which is unacceptable in a hospital operating room environment. Further, excessive amounts of the costly I—653 anesthetic can be used and lost. The present invention provides an apparatus and such a method of administration that overcomes these problems.

SUMMARY OF INVENTION

The present invention relates to an apparatus for mixing a volatile anesthetic, having a vapor pressure of about 760 mm of mercury at about 20° C., into a effective anesthetic/diluent gas mixture to be supplied to a patient, useful to monitor the flow rate of volatilized anesthetic, the flow rate of diluent gas, and the mixture ratio (i.e., the concentration of anesthetic), which apparatus comprises:

(a) a housing effective to thermally insulate the interior chamber of the apparatus from the operating room environment;

(b) a diluent gas supply;

(c) an anesthetic gas supply located within the space created by the housing;

(d) a mixing chamber within the space created by the housing which has (i) an inlet conduit, for a diluent gas supply which is external to the housing and a flowmeter, within or without the space created by the housing between the diluent gas supply and the mixing chamber;

(ii) an inlet conduit, for an anesthetic gas supply which is located within the housing and a flowmeter both within the space created by the housing, between the anesthetic gas supply and the mixing chamber; and (iii) an outlet conduit within the space created by the housing to deliver the anesthetic plus diluent gas mixture to the patient;

(e) at least one heating means to maintain the constant temperature of the components within the space created by the housing of between about 30° and 50° C. within plus or minus 1° C., and (f) at least one sensing means within the space created by the housing to accurately monitor and maintain the internal temperature of the space enclosed by the housing.

In the preferred embodiment, the diluent gas is independently selected from oxygen, air, nitrogen, nitrous oxide, or mixtures thereof.

In another aspect, the present invention relates to a method for producing an effective anesthetic/diluent vapor mixture useful for inducing rapid anesthesia in a mammal, which method comprises:

(a) maintaining a volatile anesthetic having a vapor pressure of about 760 mm of mercury at a temperature of between about 15° and 30° C.;

(b) accurately measuring an effective amount of the vapor of the anesthetic of step (a) in a flowmeter;

(c) accurately measuring an effective amount of diluent gas independently selected from the group consisting of air, oxygen, nitrogen, nitrous oxide or mixtures thereof; and (d) combining and mixing the volatile anesthetic of step (b) and the diluent gas of step (c) in a mixing chamber to produce an effective anesthetic vapor mixture to administer to a mammal, wherein in steps (a), (b), (c) and (d), all vapor components are maintained at the same temperature of between about 30° and 50° C., accurate to plus or minus 1° C.

In a preferred embodiment, in steps (a), (b), (c) and (d), the gases are heated using at least one electrically heated metal element.

In a preferred embodiment, steps (a), (b), (c) and (d) the gases are heated using at least one incandescent light bulb.

In a preferred embodiment, the temperature of the anesthetic/diluent mixture is between about 40° and 45° C.

In a preferred embodiment, the volatile anesthetic has a vapor pressure of about 760 mm of mercury at between about 15° and 30° C.

In a preferred embodiment, the volatile anesthetic is I—653, $CF_2H$—O—CFH—$CF_3$.

In a preferred embodiment, the temperature of substep (b) is maintained at about plus or minus 0.1° C.

In a specific embodiment, the present invention relates to an apparatus for mixing a volatile inhalation anesthetic having a vapor pressure of about 760 mm of mercury at between about 20° and 30° C. with a diluent gas mixture selected from oxygen, air, nitrogen, nitrous oxide, or mixtures thereof, to be supplied to a patient, which apparatus is useful to monitor the concentration and flow rate of vaporized anesthetic, the concentration and flow rate of diluent gas and the anesthetic/diluent gas mixture ratio, which apparatus comprises:

(a) a housing effective to thermally insulate the interior components of the apparatus from the operating room environment;

(b) an diluent gas supply;

(c) an anesthetic gas supply located with the space created by the housing;

(d) a mixing chamber within the space created by the housing which has:

(i) an inlet conduit for the diluent gas supply which is external to the space created by the housing and a flowmeter within or without the space created by the housing between the diluent gas supply and the mixing chamber;

(ii) an inlet conduit for the anesthetic gas supply which is located within the space created by the housing and a flowmeter both within the housing between the anesthetic gas supply and the mixing chamber; and (iii) an outlet conduit within the space created by the housing to connect to a delivery system outside the housing to deliver the anesthetic/diluent gas mixture to the patient;

(e) accurate heating means to maintain a constant temperature within the space created by the housing of between about 35° and 50° C. within plus or minus 1° C.; and (f) thermal sensing means within the housing to accurately monitor and maintain the temperature of the components within the space enclosed by the housing.

BRIEF DESCRIPTION OF THE DRAWINGS

FIG. 1 shows in partial phantom outline the overall anesthetic apparatus to volatilize a liquid having a vapor pressure of about one atmosphere at 20° C.

FIG. 2 shows in more detail the electrical circuit to heat the chamber and to control the chamber temperature.

FIG. 3 shows in more detail the anesthetic container, mixing and delivery means within the temperature controlled chamber.

FIG. 4 shows the heating means of FIG. 3 as an incandescent light bulb.

DETAILED DESCRIPTION OF THE INVENTION AND PREFERRED EMBODIMENTS

The present invention is based on the concept that heating the anesthetic to a temperature well above its boiling point will permit the production of gas (i.e., the liquid is converted into a gas. The gas produced is then metered carefully using an ordinary flowmeter. While it is still in the heated environment, the metered anesthetic is then combined with the diluent gas, as needed. At a minimum, diluent gas is needed to supply the metabolic needs of the patient for oxygen.

Referring now to FIGS. 1, 2, 3 and 4, the apparatus 10 of the present invention comprises the following parts. Container(s) 11A (and 11B) holds the liquid anesthetic 12 by means of metering valves 27 and is connected using appropriate tubing 13, 13A, 13B, 13C, 13D and 13E to a standard flowmeter 14A (obtained from, for example, Brooks Instrument Division of Emerson Electric Company, 407 West Vine Street, Hatfield, Pa. 19440).

The output 15A or 15B of the anesthetic flowmeters 14A and 14B is combined with the diluent flow 16 (i.e. as in a carburetor 17) produced by a second flowmeter 18 (or a combination of flowmeters).

All of the parts of the apparatus 10 (anesthetic containers 11A and 11B), anesthetic flowmeters 14A and 14B, carburetor 17 and connecting tubing 13, 13A to 13E, and 15A and 15B) are contained in a housing 19 (chamber or box) that is maintained at a constant temperature using a servo temperature controller and thermal sensors 23A and/or 23B. The means of heating can take a number of forms. It can be standard incandescent light bulbs 50 (e.g. 40W, 60W, 100W) or any standard type of heating element or tape 21.

The optimum temperature for the interior chamber 21 created by housing 19 is between about 40°-45° C. In this temperature range, the vapor pressure of an anesthetic 12 having a vapor pressure of about one atmosphere at 20° C. is approximately two atmospheres. This pressure minimizes the effect of ventilation back pressure on the flowmeter-setting (i.e., higher pressures of anesthetic are not needed). Also, this range of temperatures is not likely to cause any thermal injury (or burns) to the patient or the operator of the vaporizer. The knobs 22A and 22B to the needle valves controlling the flow of anesthetic through flowmeters 14A and 14B are outside the temperature controlled chamber 21. Diluent flowmeters 18 can be inside or outside chamber 21, preferably inside the housing 19.

The simple apparatus of this invention vaporizes the liquid anesthetic into a useful anesthetic gas independent of any other gas(es) being present. The apparatus of this invention has an exterior housing 19 which thermally isolates and controls the temperature of the interior components from the operating room environment. These components include the liquid anesthetic in canisters 11A and 11B, the flowmeters 14A and 14B and its connections 13 to 13E and the mixing carburetor 17. The gaseous anesthetic 12 combines with the diluent gas (or gases) 16 at elevated temperature within the space created by the housing. The anesthetic/ diluent gas mixture 25 keeps its form as a gas and is subsequently immediately administered to the patient.

Preferably, the temperature within the chamber 21 is between about 40° to 45° C.

Preferably, the anesthetic has a vapor/pressure of about 760 mm of mercury at a temperature of between about 20° and 25° C..

Preferably, the volatile anesthetic is between about 1 and 20 percent by volume of the total volume of the gases delivered to a patient.

Preferably, temperature sensing means 23A and/or 23B are placed in contact with the outer surface of the anesthetic container or within the anesthetic itself. The temperature control is within ±0.5° C., preferably about ±0.1° C.

The following examples are to be construed as being illustrative and explanatory only. They are not to be construed as being limiting in any way.

EXAMPLE 1

In a hospital operating room, the apparatus described herein is used to accurately deliver an anesthetic, $CF_2H$—O—CFH—$CF_3$, and a diluent gas of oxygen. Two canisters of anesthetic 11A and 11B (11B is the back-up canister) are placed in the apparatus described in FIGS. 1, 2 and 3. Power is supplied to the heating circuitry via switch 26. Anesthetic vapor is released from the canisters 11A and 11B in a controlled manner by opening the metering valves 27 and the safety toggle valves 28A and 28B. The housing 19 isolates the components which are heated to about 41° C. using either the light bulb 50 or a heating element or strip 21. The interior of the housing chamber is temperature controlled either by a single sensor (23) located near the center of the compartment, by two such sensors 23A and 23B attached closely but removably, each to one of the canisters 11A and 11B. If the latter is done, switch 29 is used to select the sensor attached to the canister in use at that time. This technique allows closer control of the actual agent temperature. When changing over to the other canister (if the first empties), toggling switch 29 connects the sensor on the full can to the controller. The housing 19 thermally isolates the components which are heated to about 41° C. using light bulb (50 watts). The interior of the housing chamber is temperature controlled using sensors 23° at ±0.1° C. (from Omega Engineering, Inc., P.O. Box 2669, One Omega Drive, Stamford, Conn. 06906. The anesthetic is controlled at knobs 22A and 22B and flow rate is measured using flowmeters 14A and 14B at a rate of 10 to 700 ml/min. The diluent gas enters at point 24 at a rate of 200 to 5000 ml/min. and anesthetic and diluent are mixed. The anesthetic mixture is delivered to the patient at about 210 to 5700 ml/min. for as long as is needed for the surgical procedure. Usually, the I—653 concentration is between about 1 and 20 percent by volume of the total gases delivered to the patent.

With the controlled production of the gaseous I—653, the choice of the ratios of anesthetic to diluent gas at the time of administration are those selected which are conventional in this field.

While only a few embodiments of the invention have been shown and described herein, it will become apparent to those skilled in the art that various modifications and changes can be made in the apparatus and method to effectively vaporize and deliver an inhalation anesthetic having a vapor pressure of about one atmosphere without departing from the spirit and scope of the present invention. All such modifications and changes coming within the scope of the appended claims are intended to be carried out thereby.

We claim:

1. An apparatus for mixing a volatile anesthetic, having a vapor pressue of about 760 mm of mercury at about 20° C., into a effective anesthetic/diluent gas mixture to be supplied to a patient, useful to monitor the flow rate of volatilized anesthetic, the flow rate of diluent gas and the anesthetic/diluent gas mixture ratio at an effective anesthetic concentration, which apparatus comprises:

(a) a housing effective to thermally insulate the interior of the apparatus from the operating room environment;
   (b) a diluent gas supply;
   (c) an anesthetic gas supply located within the space created by the housing;

(d) a mixing chamber within the space created by the housing which has
  (i) an inlet conduit, for a diluent gas supply which is external to the housing and a flowmeter, within or without the space created by the housing between the diluent gas supply and the mixing chamber;
  (ii) an inlet conduit, for an anesthetic gas supply which is located within the housing and a flowmeter both within the space created by the housing, between the anesthetic gas supply and the mixing chamber; and
  (iii) an outlet conduit within the space created by the housing to deliver the anesthetic plus diluent gas mixture to the patient;
(e) at least one heating means to maintain the constant temperature of the components within the space created by the housing of between about 30° and 50° C. within plus or minus 1° C., and
(f) at least one sensing means within the space created by the housing to accurately monitor and maintain the internal temperature of the space enclosed by the housing.

2. The apparatus of claim 1 wherein the heating means of subpart (e) is at least one electrically heated metal element.

3. The apparatus of claim 1 wherein the heating means of subpart (e) is at least one incandescent light bulb.

4. The apparatus of claim 1 wherein the temperature within the housing is between about 40° and 45°.

5. The apparatus of claim 1 wherein the volatile anesthetic has a vapor pressure of about 760 mm of mercury between about 15° and 30° C.

6. The apparatus of claim 1 wherein the volatile anesthetic is I—653, $CF_2H$—O—$CFH$—$CF_3$.

7. The apparatus of claim 1 wherein in subpart (e) the flowmeter for the diluent gas is outside the housing.

8. The apparatus of claim 1 wherein in subpart (f) the sensing means are thermoelectric sensors.

9. The apparatus of claim 1 wherein the temperature in subpart (e) is maintained between plus or minus 0.1° C.

10. The apparatus of claim 1 wherein the diluent gas is independently selected from oxygen, air, nitrogen, nitrous oxide or mixtures thereof.

11. A method for producing an effective anesthetic/diluent vapor mixture useful for inducing rapid anesthesia in a mammal, which method comprises:
(a) maintaining a volatile anesthetic having a vapor pressure of about 760 mm of mercury at a temperature of between about 15° and 30° C.;
(b) accurately measuring an effective amount of the vapor of the anesthetic of step (a) in a flowmeter;
(c) accurately measuring an effective amount of diluent gas independently selected from the group consisting of air, oxygen, nitrogen, nitrous oxide or mixtures thereof; and
(d) combining and mixing the volatile anesthetic of step (b) and the diluent gas of step (c) in a mixing chamber to produce an effective anesthetic vapor mixture to administer to a mammal, wherein in steps (a), (b), (c) and (d), all vapor components are maintained at the same temperature of between about 30° and 50° C., accurate to plus or minus 1° C.

12. The method of claim 11 wherein in steps (a), (b), (c) and (d), the gases are heated using at least one electrically heated metal element.

13. the method of claim 11 wherein in steps (a), (b), (c) and (d) the gases are heated using at least one incandescent light bulb.

14. The method of claim 11 wherein the temperature of the anesthetic/diluent mixture is between about 40° and 45° C.

15. The method of claim 11 wherein the volatile anesthetic has a vapor pressure of about 760 mm of mercury at between about 15° and 30° C.

16. The method of claim 11 wherein the volatile anesthetic is I—653, $CF_2H$—O—$CFH$—$CF_3$.

17. The method of claim 11 wherein the temperature of substep (b) is maintained plus or minus 0.1° C.

18. An apparatus for mixing a volatile inhalation anesthetic having a vapor pressure of about 760 mm of mercury at between about 20° and 30° C. with a diluent gas mixture selected from oxygen, air, nitrogen, nitrous oxide or mixtures thereof to be supplied to a patient, which apparatus is useful to monitor the flow rate of vaporized anesthetic, the flow rate of diluent gas and the anesthetic/diluent gas mixture ratio which provides an effective anesthetic concentration, which apparatus comprises:
(a) a housing effective to thermally insulate the interior components of the apparatus from the operating room environment;
(b) an diluent gas supply;
(c) an anesthetic gas supply located with the space created by the housing;
(d) a mixing chamber within the space created by the housing which has:
  (i) an inlet conduit for the diluent gas supply which is external to the space created by the housing and a flowmeter within or without the space created by the housing between the diluent gas supply and the mixing chamber;
  (ii) an inlet conduit for the anesthetic gas supply which is located within the space created by the housing and a flowmeter both within the housing between the anesthetic gas supply and the mixing chamber; and
  (iii) an outlet conduit within the space created by the housing to connect to a delivery system outside the housing to deliver the anesthetic/diluent gas mixture to the patient;
(e) accurate heating means to maintain a constant temperature within the space created by the housing of between about 35° and 50° C. within plus or minus 1° C.; and
(f) thermal sensing means within the housing to accurately monitor and maintain the temperature of the components within the space enclosed by the housing.

19. The apparatus of claim 18 wherein the anesthetic supply is contained in a metal canister and at least one thermal sensing means of subpart (f) is on the exterior surface of the metal canister.

20. The apparatus of claim 18 wherein at least one thermal sensing means of subpart (f) is in direct contact with the liquid anesthetic within the space created by the housing.

* * * * *